(12) United States Patent
Moss et al.

(10) Patent No.: US 6,528,317 B1
(45) Date of Patent: Mar. 4, 2003

(54) METHOD OF PROVIDING A DETECTABLE MARKER IN A FLUID

(75) Inventors: Gerald Frank Moss, Swindon (GB);
Gerald Melville Aubrey Jones, Nr. Swindon (GB)

(73) Assignee: Wrc plc (GB)

( * ) Notice: Subject to any disclaimer, the term of this patent is extended or adjusted under 35 U.S.C. 154(b) by 0 days.

(21) Appl. No.: 09/420,644

(22) Filed: Oct. 19, 1999

(30) Foreign Application Priority Data

Oct. 20, 1998 (GB) .............................................. 9822729

(51) Int. Cl.[7] .............................................. G01N 37/00
(52) U.S. Cl. ......................................... 436/56; 422/119
(58) Field of Search .............................. 436/56; 422/119

(56) References Cited

U.S. PATENT DOCUMENTS

| | | | |
|---|---|---|---|
| 2,716,961 A | | 9/1955 | Manheim et al. |
| 3,263,012 A | | 7/1966 | Nadler et al. |
| 4,800,066 A | * | 1/1989 | Sinclair et al. .............. 422/119 |
| 5,055,300 A | * | 10/1991 | Gupta ........................ 424/409 |
| 5,352,244 A | | 10/1994 | Azok |
| 5,451,505 A | * | 9/1995 | Dollinger ...................... 435/6 |

FOREIGN PATENT DOCUMENTS

| | | |
|---|---|---|
| EP | 0527850 B1 | 7/1997 |
| EP | 0657028 B1 | 7/1997 |
| GB | 2276450 | 9/1994 |
| WO | WO 90/10044 | 9/1990 |
| WO | WO 90/14441 | 11/1990 |
| WO | WO 91/17265 | 11/1991 |
| WO | 9502702 | 1/1995 |

OTHER PUBLICATIONS

UK Patent Office Examination Report dated Sep. 27, 2001.
UK Patent Office Examination Report dated Feb. 9, 2000.

* cited by examiner

*Primary Examiner*—Jill Warden
*Assistant Examiner*—Monique T. Cole
(74) *Attorney, Agent, or Firm*—Rankin, Hill, Porter & Clark LLP

(57) ABSTRACT

A method of providing a detectable marker in a fluid. The method comprises disposing in said fluid a marker composition 10 comprising a matrix material 12 having a detectable marker substance 14 incorporated therein, the matrix material 12 serving to release the marker substance 14 into the fluid over time.

16 Claims, 1 Drawing Sheet

METHOD OF PROVIDING A DETECTABLE MARKER IN A FLUID

This invention relates to a method of providing a detectable marker in a fluid. The invention also relates to a marker composition per se.

The concept of marking or tagging liquids with a marker substance (also known in the art as an "identifier" or a "tracer") such as a dye, radioactive substance or DNA, to allow their subsequent tracing, is well known. The system used to introduce the marker into the liquid depends upon the particular application. Liquids may be dosed manually or by using a dosing pump system depending upon whether a single event is to be traced or an ongoing trace is required. For example, a tank of liquid may be dosed manually with a dye to determine whether the liquid is leaking into a stream. This approach could be used where say a pollution incident has occurred and the source of the pollution is to be determined. Alternatively a longer term monitoring approach could be used whereby the liquid in the tank is continuously dosed via a dosing pump so that any pollution incident may be detected as it occurs.

Manual dosing may be acceptable for a single incident but where information is required for longer term or for intermittent events, or where manual entry is not possible, dosing by a pumped system is the only alternative method currently available. However such systems require ongoing power, are relatively complicated and therefore are susceptible to unscheduled breakdown and may not be suitable for use in some locations, for example, which are aggressive, have limited or difficult access or where many sites or different liquids are to be monitored simultaneously.

We have now found a way of releasing a marker substance into a fluid over a period of time without the need for repeated manual doses, and without the need to provide any ongoing power. Thus, the invention avoids the need for the use of sophisticated mechanical and/or electronic controlled equipment. Broadly, we achieve this by providing the marker substance in a matrix material which is selected to control the rate of release of the marker substance into the fluid.

According to one aspect of the present invention there is provided a method of providing a detectable marker in a fluid, comprising disposing in said fluid a marker composition comprising a matrix material having a detectable marker substance incorporated therein, the matrix material serving to release the marker substance into the fluid over time.

The marker substance may be released from the fluid by a number of means, including leaching, or by using properties of chemical or electrostatic affinity. When leaching is used as a release system, the matrix material may comprise a cement (typically a hydraulic cement); this could provide a long term release system, particularly in acid environments. However, we especially prefer that the matrix material is soluble in the fluid, whereby the marker substance is released as the matrix material dissolves.

In one embodiment, the marker substance is incorporated into the matrix material in such a way that the marker substance is released from the matrix material directly into the fluid, for example by dissolution of the marker substance.

In another embodiment, the marker substance is encapsulated in a capsule of a material different from the matrix material, and the encapsulated marker substance is released into the fluid from the matrix material, for example by dissolution of the matrix material. Preferably, the capsule material releases the marker substance from the capsule under different conditions than the matrix material releases the capsule material. Thus, if the capsule material is soluble in the fluid, then it is desirable that the capsule material is soluble in the fluid under different conditions from the matrix material. In this embodiment, the marker composition may include capsules made from different capsule materials, each capsule material dissolving in response to different conditions; it is also preferred that a different marker substance is encapsulated within different capsule materials. This embodiment enables the marker substance to be targeted to a location downstream of the position in which it is originally located. For example, if it is difficult to dispose the marker composition in a pipe to be tested, and the conditions in the pipe are different from the conditions in an upstream location, then release of the marker substance can be targeted to the pipe to be tested by using a capsule which will only release the marker substance in response to the conditions in the pipe to be tested.

A wide variety of different marker substances may be used. The main characteristic of the marker substance is that it should be detectable, so that the presence or absence of the marker substance can be confirmed. Thus, marker substance may be either soluble or insoluble in the fluid. When the marker substance is a dye, then its presence can be confirmed by a characteristic colour change in the fluid.

Furthermore, the marker substance may be provided on a suitable insoluble carrier, such as microspheres. The microspheres may be glass or plastics or any other suitable material which is relatively inert to the fluid.

The marker substance may contain a dye or a radioactive material, but it is especially preferred that the marker substance contains DNA molecules of one or more unique identifiable codes. Preferably, the marker substance comprises microspheres to which the DNA molecules are bonded. It is preferred that the specific gravity of the microspheres is selected to give a desired dispersion in the target fluid. Examples of such DNA coated microspheres are described in EP-A-0527850, EP-A-0657028 and EP-A-0774012.

There are a wide variety of suitable matrix materials, including soluble starches (which are especially preferred), soluble salts (particularly salts of fatty acids such as sodium stearates), and high molecular weight soluble aromatic and aliphatic compounds. Obviously, the nature of the marker material depends upon the nature of the fluid in which it is to be used and on the release system. Thus, if dissolution is the release system, the water soluble matrix materials should be used in aqueous fluids and organic soluble matrix materials should be used in organic media.

The useful life of the marker composition (i.e., the time taken before substantially all the marker substance has been released) may be anything from a few second up to several years. Typically, this time would be a matter of hours, days or weeks.

The method of the present invention preferably also includes the step of analysing a fluid sample to determine the presence or absence of the marker. This analysis may be carried out continuously or periodically. The fluid sample will be taken from a fluid which is known, or suspected, to have been in the same location as the marker composition.

According to another aspect of the invention there is provided a marker composition for releasing a detectable marker substance into a fluid, comprising a matrix material having the marker substance incorporated therein, the marker substance being releasable from the matrix material in response to contact of the matrix material with the fluid.

According to another aspect of the invention there is provided a marker composition for releasing a detectable marker substance into a fluid, comprising a matrix material having a plurality of capsules incorporated therein, each capsule containing an amount of a detectable marker substance, the capsules being releasable from the matrix material in response to contact of the matrix material with the fluid, and the marker substance being releasable from the capsule in response to a predetermined condition in the fluid.

The conditions under which the capsules are released from the composition are preferably different from the predetermined condition under which the marker substance is released from the capsules.

As mentioned above the marker substance may be a dye or a radioactive material, but it is preferred that the marker substance comprises DNA molecules having at least one unique identifying code. Preferably, the marker substance comprises microspheres to which the DNA molecules are bonded.

In some circumstances the marker composition may comprise more that one different marker substances. For example, in an embodiment the marker composition includes more than one type of capsule material, each capsule material releasing the encapsulated marker substance in response to a different condition; in this embodiment, it would be desirable to employ a different marker substance within each type of capsule material.

A support means may be provided to support the marker composition in the fluid. The support means may be, for example, an elongate, preferably flexible, support, such as a wire, tube or cord, or may be a suitable cage, vessel or bracket. In the preferred embodiment, the support means comprises a cord to which the matrix material is attached. Preferably, the matrix material has been cast around the support means.

According to another aspect of the invention there is provided a method of determining the location of the source of a pollutant fluid in a polluted fluid, comprising: disposing a marker composition as described above in each of a plurality of possible sources of the pollution, the marker substance of each marker composition being distinguishable from the marker substance in the or each other marker composition, and continuously or periodically monitoring the polluted fluid for the presence of each marker substance.

Thus, the present invention provides a system for the controlled release of one or more marker substances (tracers) over time, in which the marker substance(s) is encapsulated in a matrix material which will slowly dissolve, and is located or suspended in the fluid by an appropriate means such as a cord, wire, cage, tube, vessel, bracket or similar. The matrix material used to encapsulate the marker substance(s) depends upon the specific chemical, physical and hydraulic properties of the fluid to be marked and the tracer to be released. The matrix material dissolves into the fluid to be monitored thereby releasing the marker substance(s) into the liquid over the required period of time or event duration. The rate at which the matrix material dissolves need not be uniform but is preferably in a range suitable to allow the sufficient release of the marker substance(s) to enable subsequent detection.

The geometry, dimensions and size of the matrix material will depend upon the particular application, the properties of the fluid, the marker substance(s) to be released, the matrix material itself, and the time for which monitoring is required.

Although the invention may be used with gaseous fluids, the invention is primarily intended for use with liquid fluids, or liquid/solid fluids such as slurries and sludges (which are known as residuals in the USA and Canada). The liquids, slurries or sludges may be aqueous or non-aqueous.

The invention can be used in a number of different environments including, but not limited to, tanks, pipes, drains, sewers, gutters (especially roof gutters), etc. In one application, the marker composition may be suspended, in intermittently flowing liquid streams, such as occur in surface water drains, which are thought to discharge into a receiving water or sewer; the receiving water or sewer stream can be monitored to detect the presence or otherwise of each of the marker substance, thereby confirming whether or not the liquid streams do discharge into the receiving water or sewer. In another application, the marker composition may be suspended in tanks of liquid, such as farm slurry, which are suspected of polluting a watercourse. The watercourse may be monitored for the presence of the marker substance thereby identifying the source of the pollution. Of course, if there is thought to be more than one possible source of the pollution, then a different marker composition, each containing a different marker substance (for example, each having a different unique DNA code), may be disposed in each possible source. The identification of the specific marker substance which reaches the polluted area can then be identified, thereby allowing the source of the pollution to be uniquely identified.

Another application of the invention is to provide a marker in water supplies, especially domestic water supplies. This could may be useful when several different water companies are providing water to a common water supply. If the water supplied to a user failed a test, then the original supplier or suppliers of the water could be identified from the marker substance present. Each water company could be designated a unique marker substance to enable their water to be identified.

Reference is now made to the accompanying drawings, in which.

Figure 1:
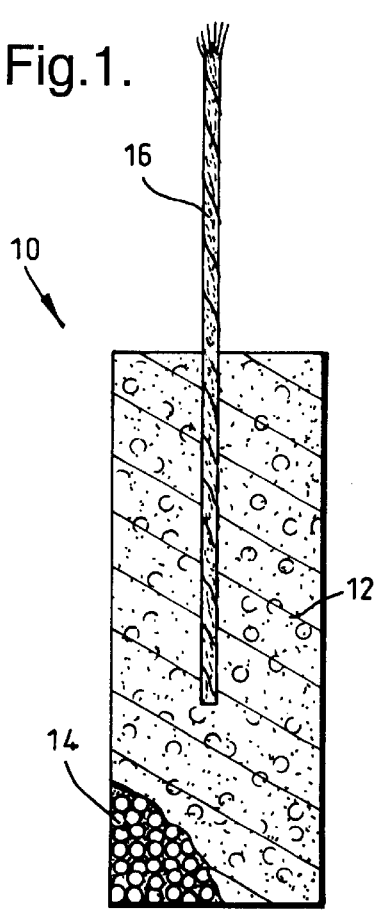
FIG. 1 is a cross sectional view of one embodiment of a marker composition according to the invention.

In FIG. 1, a first embodiment of a marker composition generally designated 10 comprises a matrix material 12 within which is incorporated particles 14 of a detectable marker substance. The matrix material 12 is cast about a flexible cord 16. The cord 16 enables the marker composition 10 to be suspended in a fluid in a tank, pipe, drain, sewer, gutter or any other desired environment. The matrix material 12 releases the particles 14 into the fluid in response to contact with the fluid. Typically, the matrix material 12 is soluble in the fluid so that the particles 14 are released by dissolution of the matrix material over a period of time.

Figure 2:
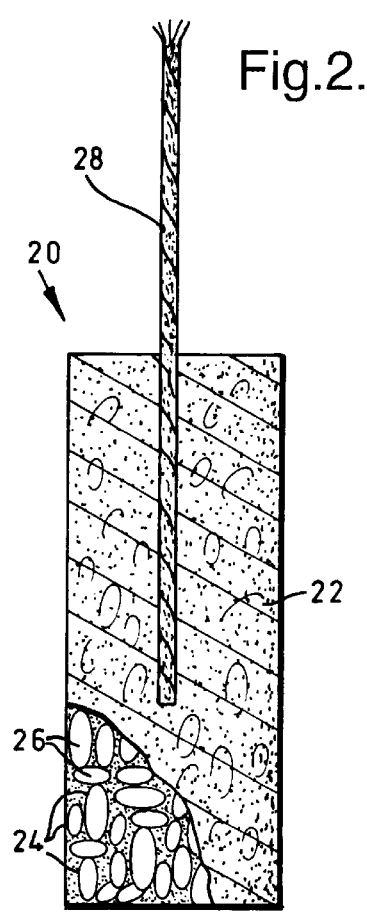
FIG. 2 is a cross sectional view of another embodiment of a marker composition according to the invention.

In FIG. 2, a second embodiment of a marker composition generally designated 20 comprises a matrix material 22 within which is incorporated a plurality of capsules 24 each of which is made of a capsule material. Each capsule 24 encapsulates a marker substance 26. The matrix material 22 is cast about a flexible cord 28. The cord 28 enables the marker composition 20 to be suspended in a fluid in a tank, pipe, drain, sewer, gutter or any other desired environment. The matrix material 22 releases the capsules 24 into the fluid in response to contact with the fluid. Typically, the matrix material 22 is soluble in the fluid so that the capsules 24 are released by dissolution of the matrix material over a period of time. The capsules are made of a material which can release the marker composition 26 therefrom under conditions different from the conditions under which the capsules 24 are released from the matrix material 22.

Figure 3:
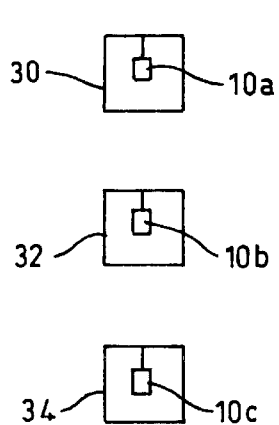
FIG. 3 is a schematic representation of a method of determining the location of the source of pollution in a river from a plurality of possible pollution sources, in accordance with an embodiment of the invention.
Figure 3:
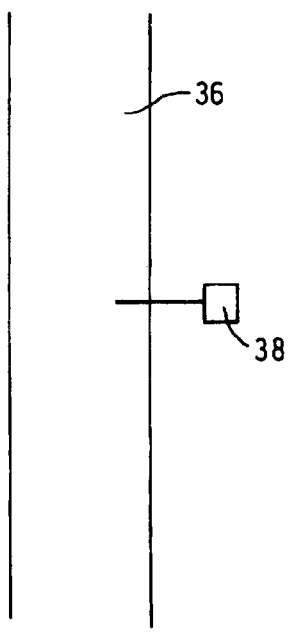

In FIG. 3 there is illustrated a method of determining the location of pollution from a plurality of possible pollution sources. FIG. 3 shows three fluid tanks 30, 32 and 34 disposed adjacent to a river 36. Each fluid tank contains the same pollutant fluid, and at least one of the tanks 30, 32, 34 is leaking the pollutant fluid into the river 36. However, it is not known which of the tanks 30, 32, 34 is leaking. In order to determine the source of the pollution three marker compositions 10a, 10b and 10c are disposed in a respective on of the tanks 30, 32 and 34. Each marker composition 10a, 10b and 10c is identical to the marker composition 10, but contains different marker substances 14. The river water is monitored with a monitor 38 in order to determine the presence or absence of the marker substances, thereby making it possible to identify the source of the pollution.

It will be appreciated that the invention described above may be modified.

What is claimed is:

1. A method of providing a detectable marker in a fluid, comprising disposing in said fluid a marker composition comprising a matrix material having a detectable marker substance incorporated therein, the matrix material serving to release the marker substance into the fluid over time, wherein the detectable marker substance is encapsulated in a capsule formed of a material different from the matrix material, and the capsule is released into the fluid from the matrix material.

2. A method according to claim 1, wherein the capsule releases the detectable marker substance therefrom under different conditions than the conditions under which the matrix material releases the capsule.

3. A method according to claim 1, wherein the matrix material is soluble in the fluid, whereby the capsule is released as the matrix material dissolves, and the capsule material is soluble in the fluid under different conditions than the matrix material.

4. A method according to claim 1, wherein the marker composition includes a plurality of capsules made from different capsule materials, and wherein each of said different capsule materials dissolves in response to different conditions.

5. A method according to claim 4, wherein the marker composition comprises at least two different detectable marker substances, each of which is encapsulated within a different capsule material.

6. A method according to claim 1, wherein the marker substance includes DNA molecules of one or more unique identifiable codes.

7. A method according to claim 6, wherein the marker substance comprises microspheres to which the DNA molecules are bonded.

8. A marker composition for releasing a detectable marker substance into a fluid, comprising a matrix material having a plurality of capsules incorporated therein, each capsule containing an amount of the marker substance, the capsules being releasable from the matrix material in response to contact with of the matrix material with the fluid, and the marker substance being releasable from the capsule in response to a predetermined condition in the fluid.

9. A marker composition according to claim 8, wherein the marker composition includes more than one type of capsule material, each capsule material releasing the encapsulated marker substance in response to a different condition.

10. A marker composition according to claim 9, wherein a different marker substance is encapsulated within each type of capsule material.

11. A marker composition according to claim 8, wherein the conditions under which the capsules are released from the matrix material are different from the predetermined condition under which the marker substance is released from the capsules.

12. A marker composition for releasing a detectable marker substance into a fluid, comprising a matrix material having the detectable marker substance incorporated therein, the marker substance being releasable from the matrix material in response to contact of the matrix material with the fluid, wherein the marker substance comprises DNA molecules having at least one unique identifiable code.

13. A marker composition according to claim 12, wherein the marker substance comprises microspheres to which the DNA molecules are bonded.

14. A marker composition for releasing a detectable marker substance into a fluid, comprising a matrix material having the detectable marker substance incorporated therein, the marker substance being releasable from the matrix material in response to contact of the matrix material with the fluid, further comprising means to support the marker composition in the fluid.

15. A marker composition for releasing a detectable marker substance into a fluid, comprising a matrix material having the detectable marker substance incorporated therein, the marker substance being releasable from the matrix in response to contact of the matrix material with the fluid, and means to support the marker composition in the fluid, wherein the support means comprises a cord to which the matrix material is attached.

16. A marker composition according to claim 14, wherein the matrix material has been cast around the support means.

* * * * *